US012765827B2

(12) United States Patent
Kanagaratnam et al.

(10) Patent No.: US 12,765,827 B2
(45) Date of Patent: Oct. 20, 2026

(54) ELECTROPHYSIOLOGICAL CATHETER SYSTEMS

(71) Applicant: IMPERIAL COLLEGE INNOVATIONS LTD., London (GB)

(72) Inventors: Prapa Kanagaratnam, London (GB); Emmanuel Mic Drakakis, London (GB); Nicholas Linton, London (GB); Simos Koutsoftidis, London (GB)

(73) Assignee: IMPERIAL COLLEGE INNOVATIONS LTD., London (GB)

( * ) Notice: Subject to any disclaimer, the term of this patent is extended or adjusted under 35 U.S.C. 154(b) by 524 days.

(21) Appl. No.: 17/635,563

(22) PCT Filed: Aug. 14, 2020

(86) PCT No.: PCT/GB2020/051951

§ 371 (c)(1),
(2) Date: Feb. 15, 2022

(87) PCT Pub. No.: WO2021/028699

PCT Pub. Date: Feb. 18, 2021

(65) Prior Publication Data

US 2022/0296148 A1 Sep. 22, 2022

(30) Foreign Application Priority Data

Aug. 15, 2019 (GB) ...................................... 1911731

(51) Int. Cl.
*A61B 5/287* (2021.01)
*A61B 5/00* (2006.01)
(Continued)

(52) U.S. Cl.
CPC .............. *A61B 5/287* (2021.01); *A61B 5/364* (2021.01); *A61B 5/7217* (2013.01);
(Continued)

(58) Field of Classification Search
None
See application file for complete search history.

(56) References Cited

U.S. PATENT DOCUMENTS 5,350,401 A * 9/1994 Levine ................. A61N 1/3712 607/4
6,035,232 A 3/2000 Thong et al.
(Continued)

FOREIGN PATENT DOCUMENTS

EP 2591722 5/2013
JP 2014023870 2/2014
(Continued)

OTHER PUBLICATIONS

Combined Search and Examination Report for Application No. GB1911731.6 dated Feb. 14, 2020, 5 pages long.
(Continued)

*Primary Examiner* — Erica S Lee
(74) *Attorney, Agent, or Firm* — Wegman Hessler

(57) ABSTRACT

Apparatus for electrophysiological studies comprises: at least one output channel (206); a plurality of detection channels (210, 212, 214); and control means (202). The at least one output channel includes a stimulation channel. The control means (202) is arranged to provide a stimulation signal to the stimulation channel and to process detection signals from the detection channels thereby to identify ectopy events in the detection signals.

13 Claims, 15 Drawing Sheets

(51) Int. Cl.
*A61B 5/364* (2021.01)
*A61N 1/36* (2006.01)

(52) U.S. Cl.
CPC ........ *A61B 5/7225* (2013.01); *A61N 1/36017* (2013.01); *A61N 1/36114* (2013.01); *A61B 5/4035* (2013.01)

(56) References Cited

U.S. PATENT DOCUMENTS

| | | | | |
|---|---|---|---|---|
| 6,101,416 | A | 8/2000 | Sloman | |
| 6,205,357 | B1 * | 3/2001 | Ideker | A61N 1/3622 607/15 |
| 2004/0088019 | A1 * | 5/2004 | Rueter | A61N 1/3712 607/27 |
| 2007/0162079 | A1 * | 7/2007 | Shemer | A61N 1/3627 607/9 |
| 2009/0099468 | A1 * | 4/2009 | Thiagalingam | A61B 5/349 600/515 |
| 2013/0066222 | A1 * | 3/2013 | Rosenberg | A61B 5/363 600/509 |
| 2013/0158621 | A1 * | 6/2013 | Ding | A61N 1/37 607/17 |
| 2016/0166310 | A1 * | 6/2016 | Stewart | A61B 18/1492 606/34 |
| 2017/0161896 | A1 * | 6/2017 | Blake, III | G06T 7/11 |
| 2018/0326215 | A1 * | 11/2018 | Ghosh | A61N 1/3756 |

FOREIGN PATENT DOCUMENTS

| | | |
|---|---|---|
| WO | 2010/058372 | 5/2010 |
| WO | 2017/214638 | 12/2017 |

OTHER PUBLICATIONS

International Search Report and Written Opinion for International Patent Application No. PCT/GB2020/051951 dated Jan. 18, 2021, 20 pages long.

Phang Boon Lim et al., "Intrinsic Caridac Autonomic Stimulation Induces Pulmonary Vein Ectopy and Triggers Atrial Fibrillation in Humans", Journal of Cardiovascular Electrophysiology, vol. 22, No. 6, Jan. 15, 2011, pp. 638-646.

* cited by examiner

Vin (1V offset)
x10^-3
voltage/V
time/s

Vin + Continuous HFS
voltage/V
time/s

Artifact reduction AFE output
voltage/V
time/s

ELECTROPHYSIOLOGICAL CATHETER SYSTEMS

CROSS REFERENCE TO RELATED APPLICATIONS

This application is a national phase of International Patent Application No. PCT/GB2020/051951 filed Aug. 14, 2020, which claims the priority filing benefit of Great Britain Patent Application No. 1911731.6 filed Aug. 15, 2019, which are incorporated herein by reference in their entireties.

FIELD OF INVENTION

The present invention relates to electrophysiological catheter systems, for example for use in the treatment of atrial fibrillation. It has particular application in the location and ablation of sources of atrial fibrillation.

BACKGROUND OF THE INVENTION

Atrial fibrillation (AF) is the most common cardiac arrhythmia experienced worldwide. The condition affects primarily people over the age of 50 and therefore its prevalence is expected to increase in the future due to the rising trends in average age of populations. Pulmonary Vein Isolation (PVI) is an alternative to pharmaceuticals as a treatment for the condition, with a current 50-70% success rate. PVI involves the ablation of tissue around all four pulmonary veins to isolate the left atrium from known external AF inducing electrical activity.

Ganglionated Plexi (GP) sites are regions of the autonomic nervous system inside the left atrium where AF-type events have been shown to originate from. These sites are not specifically targeted by PVI. Experimental GP-based treatment has been performed which involves ablation only at the active GP sites with the aim of eliminating the AF inducing pathways inside the left atrium. Preliminary results from human trials indicate that this method can be as effective as PVI whilst using much lower ablation energy; damaging lower volumes of tissue.

GP sites involved in AF can only be identified using specific electrical stimuli to induce AF-related events, as the number and location of the active sites is patient-dependent. There is no equipment currently available dedicated to performing GP stimulation, which results in the process of identifying and classifying the GP sites being laborious, inconsistent and time consuming.

A direct consequence of the unique stimuli used for cardiac applications, including GP identification, is the deterioration of recorded signals due to stimulus artefacts; especially when recording from electrodes located near the stimulation sites. This effect results from the high amplitude stimuli, required to affect the autonomic nervous system, completely saturating any recording instrumentation sensitive enough to pick up the local tissue response.

SUMMARY OF THE INVENTION

The present invention provides apparatus for electrophysiological studies, the apparatus comprising a stimulation channel, a plurality of detection channels, and control means. The control means may be arranged to provide a stimulation signal to the stimulation channel and to process detection signals from the detection channels thereby to identify ectopy events in the detection signals.

The apparatus may further comprise one or more further stimulation channels, and the control means may be arranged to provide a further stimulation signal for each of the further stimulation channels.

The control means may be further arranged to identify ventricular activation events in the detection signals.

The control means may be arranged to control the stimulation signal in response to the outcome of the processing of the detection signals. For example the control means may be arranged to stop producing the stimulation signal in response to detection of a predetermined number of ectopy events. The predetermined number may be one.

The detection channels may include an atrial channel and at least one reference channel. The control means may be arranged to process the detection signal from the at least one reference channel to identify ventricular activation events. The control means may be arranged thereby to distinguish between ventricular activation events and ectopy events in the detection signal from the atrial channel.

The detection channels may include a plurality of atrial channels. The control means may be arranged to process a detection signal from each of the atrial channels. The control means may be arranged to identify an event as an ectopy event only if it is detected in the detection signal from each of the atrial channels.

The control means may be arranged to determine the timing of an ectopy event on each of said plurality of atrial channels. The control means may be arranged, from the timings, to locate the source of the ectopy event.

The apparatus may further comprise an atrial catheter. The atrial channel may be connected to at least one electrode on the atrial catheter. The apparatus may further comprise a ventricular catheter. One of the at least one reference channels may be connected to at least one electrode on the ventricular catheter. The apparatus may further comprise an ECG electrode set. One of the at least one reference channels may be connected to the ECG electrode set.

The at least one output channel may include a pacing channel. The pacing channel may be the stimulation channel or it may be a separate channel. The control means may be arranged to provide a pacing signal to the pacing channel.

The control means may be arranged to identify ventricular activation events that are caused by the pacing signal. The control means may be arranged to modify or stop the pacing signal in response to the identification of a predetermined number of ventricular activation events that are identified as caused by the pacing signal.

The control means may be arranged to operate in a ventricular activation test mode, or to perform a ventricular activation test, in which the pacing signal is output without the stimulation signal. The number of ventricular activations detected during the test may be compared with a threshold number to determine whether the test is passed or failed. If the test is passed the control means may enable the stimulation signal. If the test is failed, the stimulation signal may be inhibited. For example a user interface may only enable a user to start the stimulation signal if the test has been passed.

The control means may be arranged to identify ventricular events. The control means may be arranged to measure a delay between consecutive ventricular events. The control means may be arranged to determine whether the delay exceeds a predetermined time period. The control means may be arranged to determine, from the delay, the presence of one or more atrioventricular node slowing GPs.

The stimulation signal may comprise a plurality of stimulation pulses, which may be arranged in groups or may be output in a continuous sequence, for example at a constant frequency.

The pacing signal may comprise a pacing pulse. The pacing pulse may precede each of said groups of stimulation pulses.

The control means may be operable in an ectopy triggering mode in which the system is arranged to produce the pacing pulses and the groups of stimulation pulses, and an atrioventricular node slowing mode in which the system is arranged to produce the stimulation pulses without the pacing pulses.

The control means may comprise a user interface arranged to enable a user to select one of the modes and to adjust at least one parameter of the stimulation signal or the pacing signal.

Each of the stimulation pulses may be a bipolar voltage pulse.

The control means may be arranged to define a target current and to control the stimulation signal, during each of the stimulation pulses, or between the stimulation pulses, to achieve the target current.

The stimulation signal may be applied across two stimulation electrodes. For example it may be applied as a voltage difference between the two electrodes. The control means may be arranged to control the impedance between the stimulation electrodes between the stimulation pulses thereby to control an offset voltage between the electrodes. For example the control means may be arranged to reduce the impedance between the electrodes for the periods between the stimulation pulses.

The apparatus may further comprise artefact reduction means arranged to reduce the effect of the pacing signal on the detection signal. The artefact reduction means may comprise at least one analogue component, and/or it may comprise digital signal processing means.

The invention further provides apparatus for electrophysiological studies, the apparatus comprising: a stimulator output channel; a plurality of detection channels; and control means arranged to provide a stimulation signal to the output channel and to process detection signals from the detection channels, wherein at least one of the recording channels comprises a hardware tunable notch filter. The control means may be arranged to generate the stimulation signal at one of a plurality of stimulation frequencies and to tune the notch filter to filter out components of the detection signal of the at least one detection channel at said one of the stimulation frequencies.

The notch filter may be arranged to filter out components of the detection signal of the at least one recording channel at at least one harmonic of said one of the stimulation frequencies. This may be useful for example for detectors which are close to a stimulation electrode of the system.

At least one of the detection channels may not include a hardware tunable notch filter. This may be suitable for a detector which is remote from the stimulation electrode.

The control means may be arranged to select said one of the stimulation frequencies in response to a user input.

BRIEF DESCRIPTION OF THE DRAWINGS

FIG. 16*b* is the detection signal of FIG. 16*a* with HFS stimulation pulses added in;

FIG. 17*a* is a detection signal used in a simulation of the system of FIG. 15*a;*

FIG. 17*b* is the detection signal of FIG. 16*a* with continuous HFS stimulation added in; and FIG. 17*c* is the corresponding simulated output of the system of FIG. 15*a*.

DESCRIPTION OF EMBODIMENTS

Figure 1:
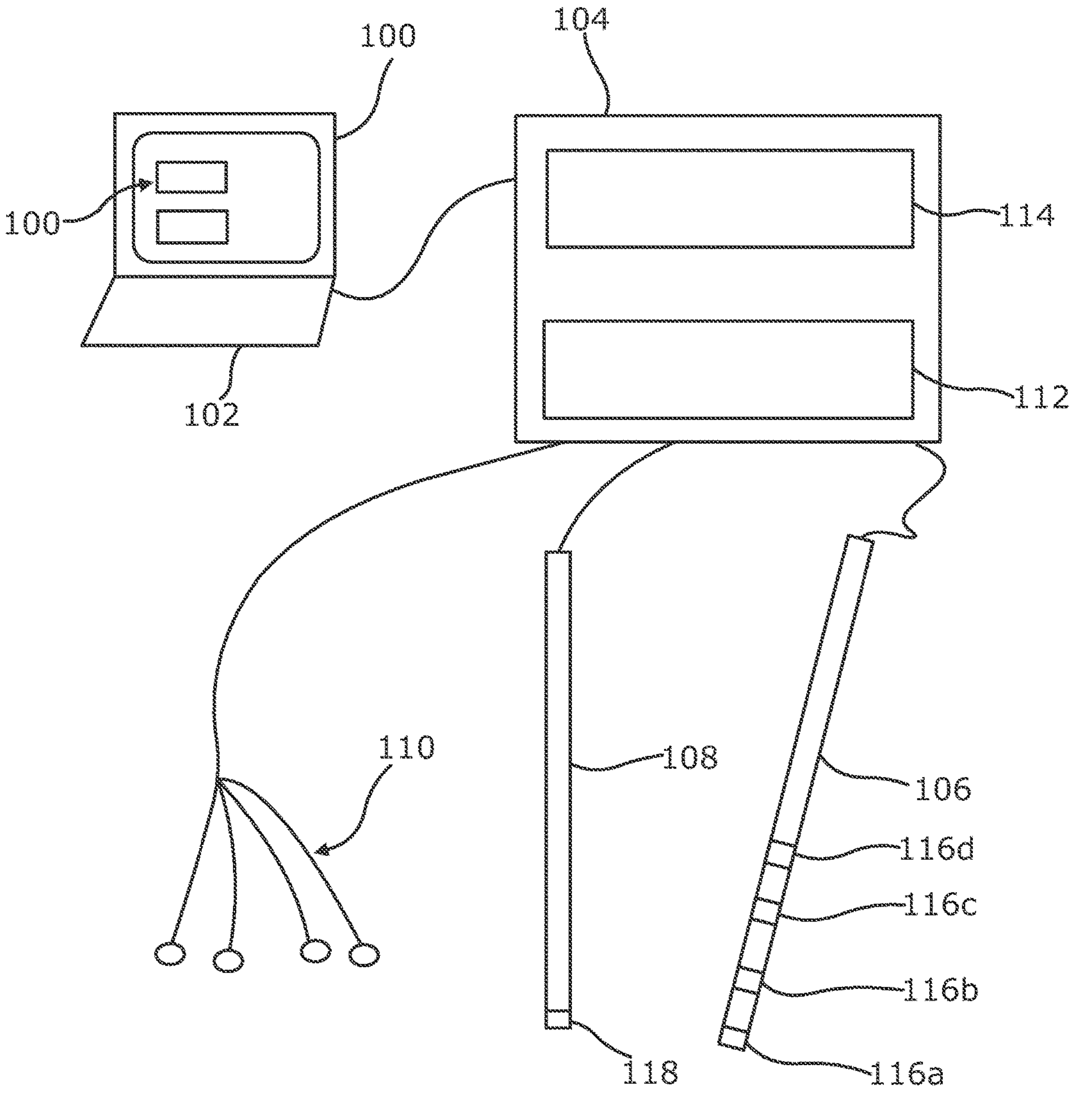
FIG. 1 is a schematic diagram of an electrophysiological system according to an embodiment of the invention.

Referring to FIG. 1, the system may comprise a user interface 100 which may be in the form of a PC or laptop computer 102, a control system 104, a stimulator and one or more detectors. The detectors will typically be in the form of one or more catheters which may for example include an atrial probe 106 and a ventricular probe 108, and an ECG electrode set 110. The stimulator may comprise a separate probe, or may be one of the detector probes, specifically it may be the atrial probe 106 which may therefore comprise stimulation and detection electrodes. The control system may comprise a cardiac mapping system 112 which is arranged to generate a 3D model of the cardiac chambers and track in real time the position of the atrial and ventricular probes 106, 108, so that measurements made using the probes can be mapped onto the 3D model of the heart. Such systems are well known, such as the Biosense Webster Carto 3 system. The control system may further comprise a processing unit 114, in the form of a hardware signal processing module, which is arranged to process signals received from the atrial and ventricular probes 106, 108. The signal processing module 114 may further be arranged to generate a stimulation signal for transmission to one of the probes which acts as the stimulator. The computer 102 may run software that provides the user interface for the system and controls parameters of the stimulation signals.

The atrial probe 106 has a number of electrodes 116 spaced along its length. One of these 116*a* may be a stimulation electrode, or pair of electrodes, and the others 116*b*, 116*c*, 116*d* may be detection electrodes, or detection electrode pairs. The arrangement of the electrodes will depend on a number of factors, including whether unipolar or bipolar signals are used. If the system is operating in unipolar mode, a reference electrode will also be provided as a patch on the surface of the body and the voltage on each of the electrodes 116*a*-116*d* on the probe is measured relative to the voltage of the reference electrode. If the system is operating in bipolar mode, then the voltage difference between the two electrodes in each pair is measured.

Figure 2:
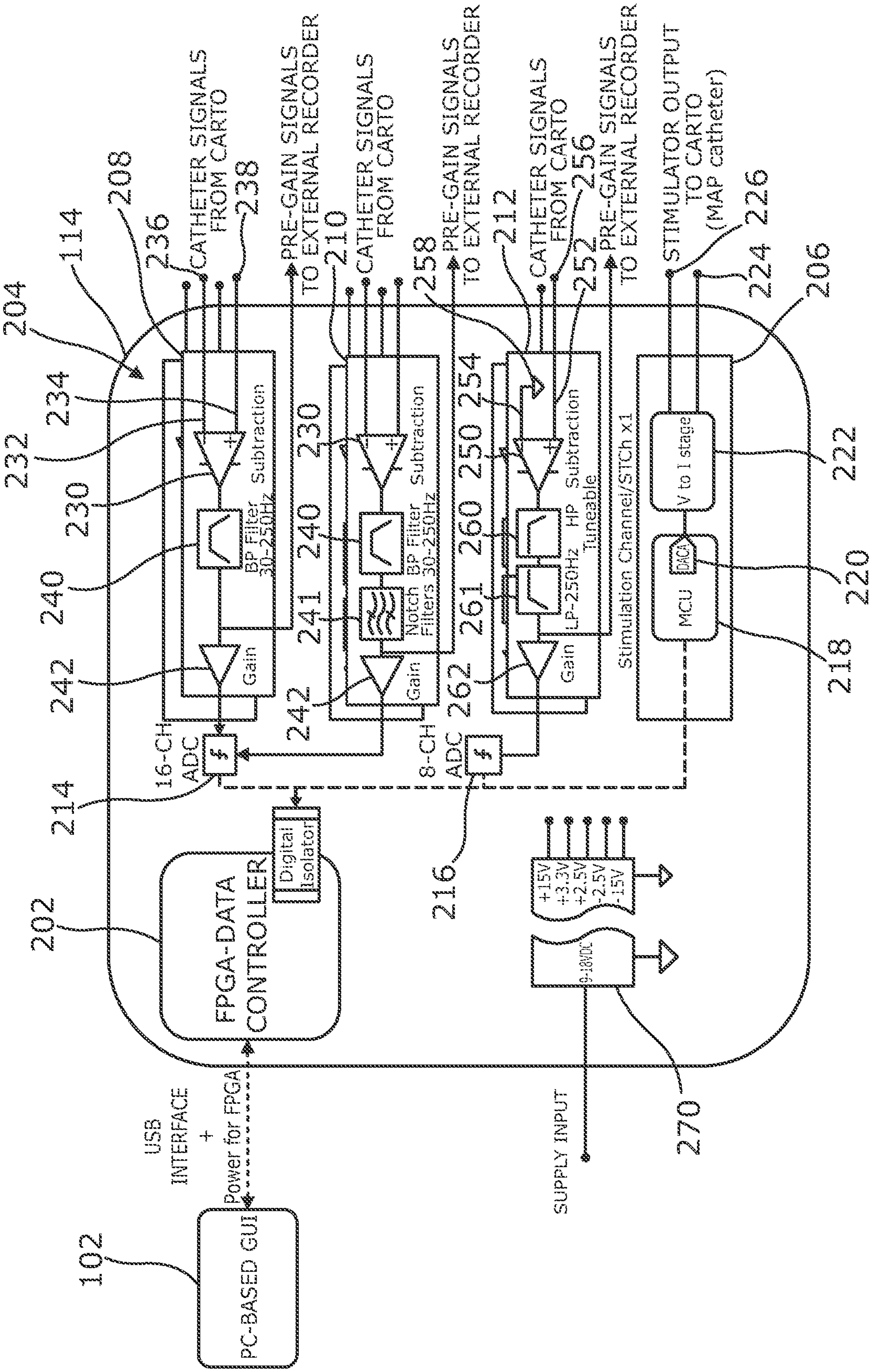
FIG. 2 is functional block diagram of the hardware components of the processing system of the electrophysiological system of FIG. 1.

Referring to FIG. 2, the processing unit 114 may comprise a data controller 202 and a number of detection channels 204 and a stimulation channel 206. The detection channels 204 may include one or more groups 208, 210 of bipolar channels arranged to receive bipolar detection signals across two electrodes, and one or more groups 212 of unipolar channels. Each of the detection channels typically provides filtering and amplification of the detection signals as will be described in more detail below. Each of the detection channels 208, 210, 212 also typically operates in the analogue domain and the filtering and amplification is provided by a number of hardware components. Each of the detection channels 208, 210, 212 may therefore be connected to the data controller 202 via an analogue-to-digital converter (ADC) 214, 216. The stimulation channel is arranged to receive a digital stimulation signal from the data controller 202. For example it may comprise a micro-controller unit (MCU) 218 including a digital-to-analogue converter 220 arranged to receive the digital stimulation signal and convert it to an analogue stimulation signal. It may also comprise a V to I stage 222, which is arranged to receive the analogue stimulation signal as an input of varying voltage and control the current of the analogue stimulation signal so that it varies with the voltage of the input. Various ways of achieving this are known in the art.

Each of the detection channels of one of the groups 208 of bipolar detection channels may comprise a subtraction unit 230, such as a comparator, having two inputs 232, 234 each connected to a respective one of the two input terminals 236, 238 of the channel, and an output in the form of a difference signal that varies with the difference between the signals on the two input terminals 236, 238. The channel may further comprise a band pass filter 240 connected to the output of the subtraction unit 230, and arranged to filter the difference signal so as to pass only components of that signal within frequency band. For example the filter may pass signals with frequencies in the range from 30 to 250 Hz. The output of the band pass filter 240 may be connected to the input of an amplifier 242 which is arranged to amplify the filtered difference signal. The output of the amplifier 242 is connected to the ADC 214 which is arranged to digitize the amplified filtered difference signal and input it to the data controller 202. These channels are suitable for detection signals that will not include significant interference from the stimulation pulse. Examples may include electrodes on the ventricular probe 108 or the ECG electrode set, and electrodes on the atrial probe 106 which are remote from the stimulation electrodes 116*a*.

Each of the detection channels of another one of the groups 210 of bipolar detection channels may include all of the components of the first group 208, which will not be described again and are indicated by the same reference numerals, but may also comprise one or more notch filters 241 each of which is arranged to filter out components of the detection signals in a narrow band about a predetermined frequency. The notch filter frequencies may be set to the frequency of the stimulation signal and/or one or more harmonics of the frequency of the stimulation signal as will be described in more detail below. The notch filters 241 also may be tunable so that they can be adjusted to match the stimulation signal if the frequency of the stimulation signal is varied. The notch filters 241 may be arranged between the subtraction unit 230 and the amplifier 242, for example connected between the output of the band pass filter 240 and the input of the amplifier 242. These channels are suitable for detection signals that will include significant interference from the stimulation pulse. Examples may include electrodes on the atrial probe 106 close to the stimulation electrodes 116*a*. However it will be appreciated that the notch filters may be included for all detection signals.

Each of the unipolar detection channels 212 may comprise a subtraction unit 250, such as a comparator, having two inputs 252, 254 one of which 252 is connected to the unipolar input terminal 256 of the channel and the other of which 254 is connected to a reference voltage 258, such as a reference electrode on the body surface or an intra-cardiac reference electrode. The subtraction unit 250 may therefore produce an output in the form of a unipolar difference signal that varies with the difference between the signal on the input terminal 256 and the reference voltage 258. The channel may further comprise filter components, such as a high pass filter 260 and a low pass filter 261 connected in series to the output of the subtraction unit 250, and arranged to filter the unipolar difference signal so as to pass only components of that signal within a frequency band between the cut-off frequency of the high pass filter 260 and the cut-off frequency of the low pass filter 261. For example the low pass filter 261 may pass signals with frequencies above 250 Hz and the low pass filter may be tunable have a variable cut-off frequency. The output of the low pass filter 261 may be connected to the input of an amplifier 262 which is arranged to amplify the filtered unipolar difference signal. The output of the amplifier 262 may be connected to the ADC 216 which is arranged to digitize the amplified filtered difference signal and input it to the data controller 202.

Each of the detection channels 208, 210, 212 may comprise an output connected to the respective channel, for example between the filters in the channel and the amplifier in the channel, which is arranged for connection to an external recorder. This allows the filtered detection signals, for example the pre-gain detection signals as shown in FIG. 2, to be output for use with other electrophysiological systems.

The processing unit 114 may further comprise a bipolar power supply module 270 arranged for connection to a DC power supply. The power supply module 270 may be arranged to output positive or negative voltage power signals at a number of different voltages. The power supply module 270 is connected to the stimulation channel 206 so that the stimulation signals can be varied between maximum positive and negative voltages, producing a bipolar stimulation signal.

The computer 102 is connected to the data controller 202, for example by a USB interface, and may also provide power to the data controller 202. The computer 102 is arranged to run software that enables it to act as a graphical or other user interface for the system. For example the software may enable a user to set various parameters of the system as will be described in more detail below.

In operation, a user can set appropriate parameters of the stimulation signal, such as peak voltage or current, pulse length and pulse frequency, via the user interface 100, which is then arranged to communicate those parameters to the control system 104. The data controller 202 is arranged to generate from the parameters a digital stimulation signal which it then transmits to the stimulation channel 206 where it is converted to an analogue stimulation signal which is output via the stimulation terminals 224, 226 of the processing unit 114, and via the mapping system 112, to two of the electrodes on the atrial probe 106, or a dedicated stimulation probe if appropriate. The stimulation signal maybe arranged, for example, to stimulate activity in the heart, such as by stimulating any ganglionated plexi. The resulting activity, or indeed any activity, in the heart, can generate electrical signals in each of the probes 106, 108 and the ECG electrode set 110, which are input, via the mapping system 112, to the terminals of the detection channels 208, 210, 212. Depending on the requirements for a particular operation, the detection signals from the atrial probe 106, the detection signals from the ventricular probe 118, and/or the detection signals from the ECG electrode set 110 are input on one or more of the detection channels 208, 210, 212, where they are filtered, amplified and digitized, before being transmitted to the computer 102. The computer 102, using appropriate software, is arranged analyse the digital detection signals to determine the location of any GP sites detected, and provide feedback or analysis to the user as appropriate. For example the system may be arranged to build up a map of the GP locations in the left atrium as the atrial probe is moved around the atrium, so that the map can be used subsequently to guide ablation. Alternatively, or in addition, the location of a detected GP site can be determined within a few seconds, and so ablation of each detected site may be carried out when it is detected.

It will be appreciated that the system of FIGS. 1 and 2 may be operated in a variety of modes and some of those will be described as examples. For example, the system may be arranged to deliver, via the stimulation probe 206, standard pulse trains that are used for patients undergoing Electrophysiology Studies with Programmed Stimulation. Examples, are the ability to provide bursts (e.g. 8 beats at 250 ms intervals), or burst with an 'extra' (e.g. 8 beats at 400 ms intervals followed by an extra beat at 300 ms).

The system may be arranged to provide autonomic stimulation. For example in one mode the system may be arranged, when the patient is in sinus rhythm, to detect ganglionated plexi that trigger ectopy. In another mode the system may be arranged, when the patient is in atrial fibrillation, to detect ganglionated plexi that slow the atrioventricular node.

Mode 1 Detection of Ectopy-Triggering GPs

Figure 3:
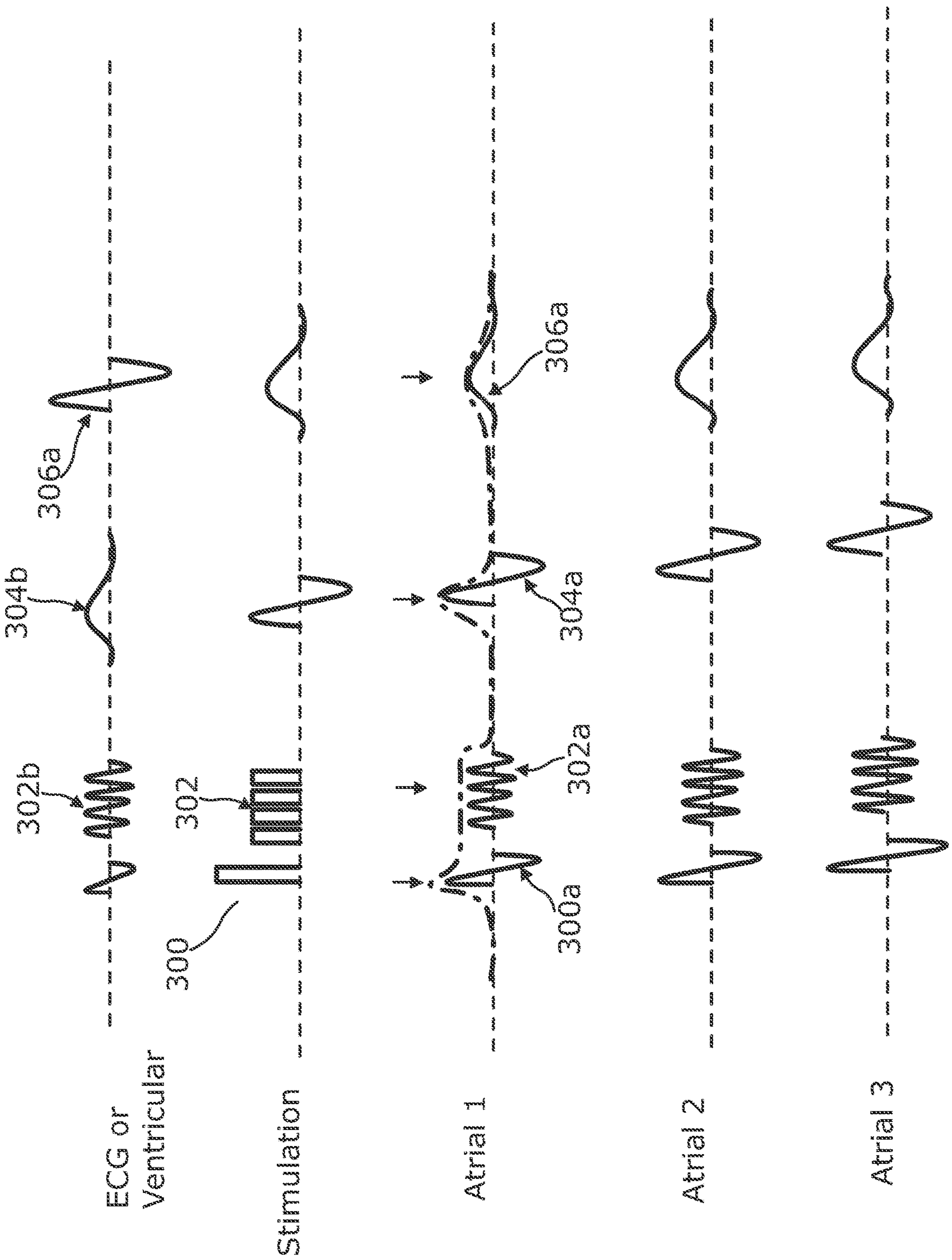
FIG. 3 shows the signals on different channels of the system of FIG. 2.

In one mode of operation the system may be arranged to produce high frequency stimulation pulses to stimulate ectopy-triggering GPs, and to analyse the detection signals received on one or more of the detectors to detect the presence of a GP and/or determine the location of each GP. Referring to FIG. 3, the stimulation signal may comprise a pacing pulse 300 and a group 302 of stimulation pulses 303. These pulses may be single phase as shown in FIG. 3 or they may be biphasic. If the pulses are single phase the pacing pulse 300 is typically a single short pulse and the stimulation pulse group 302 typically a short group of individual pulses 303 at a stimulation pulse frequency. These pulses 300, 302 are generated and transmitted on the stimulation channel 206, and therefore transmitted into the atrium through the stimulation electrodes 116*a* of the atrial probe. Each stimulation pulse 302 may trigger a GP in the atrium which produces ectopy, i.e. a premature activation originating from the GP in the atrium. This pattern of stimulation pulses is referred to as synchronous stimulation. However ventricular events, i.e. events resulting from ventricular activation, may also occur. These are not caused by the GP and therefore need to be distinguished from the ectopy.

The pacing pulse 300 will produce a corresponding pulse 300*a* in the detection signal on each of the detection channels, which will in general appear as a biphasic pulse, even for monophasic stimulation pulses, as a result of the filtering in the detection channels. It should also be noted that as the output of the stimulator is galvanically isolated from the detector, the reference potentials on the channels may not be at the same voltage. The magnitude of the detected pacing pulse 300*a* will depend on the location of the electrode at which it is generated, but provided it can be detected on each of the channels it can be used in the analysis of the detection signals. Similarly the stimulation pulse group 302 will produce a corresponding biphasic pulse group 302*a* on each of the detection channels. These pulses 300*a*, 302*a* will generally be weaker in the detection signals from the ECG electrodes 110 or ventricular probe 118. For any detection signals that are received on one of the channels 210 including notch filters 241, those notch filters 241 will of course filter out the stimulation pulse group 302*a* from the detection signal. In order to achieve that, as discussed above, the notch filters are adjusted to filter out the fundamental frequency of the stimulation pulse group 302 and at one or more harmonics of that fundamental frequency. For example the first three or four harmonics may be filtered out separately by the adjustable notch filters.

In response to the stimulation pulse 302, atrial ectopic events may be triggered. These can be detected and used to detect and locate ectopy-triggering GPs. Also ventricular events may be triggered. These need to be distinguished from atrial ectopic events. Atrial ectopic events will produce a pulse 304*a* in each atrial detection signal, i.e. the detection signals from the detection electrodes on the atrial probe 104, and also a pulse 304*b* in the ventricular detection signal, i.e. the detection signal from the ventricular probe 108, and the ECG detection signal, i.e. the detection signal from the ECG electrodes. This atrial ectopic pulse will be relatively strong in the atrial detection signals and relatively weak in the ECG and ventricular detection signals. Ventricular events will also be detected, but these will appear as a relatively strong ventricular pulse 306*b* in the ventricular detection signal and a relatively weak pulse 306*a* in the atrial detection signals.

In order to detect and classify the various pulses in each of the detection signals, the signal is processed using an algorithm which is part of the software running on the computer 102. Firstly, in order to identify potentially relevant events, each signal is put through a Canny edge detector, and then rectified and filtered. The result is as shown by the broken line for the first atrial detection signal in FIG. 3. Each peak, i.e. maximum, in the rectified filtered edge detector signal, that exceeds a threshold, is identified as an event, as shown by the vertical arrows in FIG. 3. The events are then classified by determining the timing of events in the different detection signals, and comparing them with each other and with the timing of the pacing and stimulation pulses.

Figure 4:
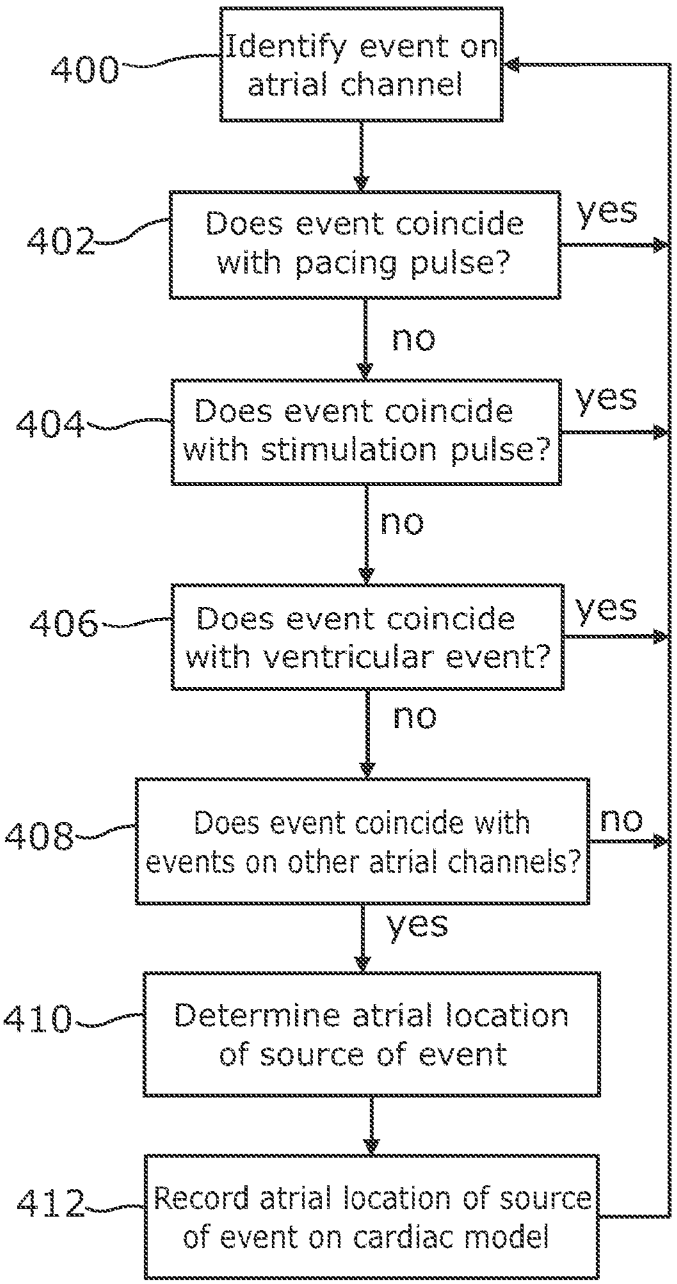
FIG. 4 is a flow diagram showing a mode of operation of the system of FIG. 1.

Referring to FIG. 4, a possible process for classifying events will now be described. After an event in the atrial detection signal on one of the detection channels is identified at step 400 using the Canny edge filter as described above, a determination is made at step 402 whether or not the event is a pacing pulse. The timing of the pacing pulses 300 is known. Therefore, all sensed events that coincide, to within a predetermined time period, with the transmission of a pacing pulse, are excluded from classification as due to atrial ectopy. For example there may be a 'blanking period' of 20 ms for each pacing pulse during which any events in the detection signals are omitted from further analysis. If the event is identified as a pacing pulse, the process returns to step 400 to identify another event. If it is not, then the process proceeds to the next step 404 which is to determine whether the event is a stimulation pulse. The timing of the stimulation pulses is also known, and if the event coincides, to within a predetermined period, with transmission of a stimulation pulse, it is identified as a stimulation pulse, and the process returns to step 400 to identify another event. If the event is not identified as a stimulation pulse, then the process proceeds to step 406 which is to determine whether the event is a ventricular event.

In order to identify ventricular events, the surface ECG signals, or a ventricular catheter placed directly inside the ventricle, can be used to detect ventricular events. Various methods of doing this are known in the art. When a ventricular event is detected in the ECG or ventricular detection signals, any events detected on the atrial channels that coincide with the ventricular event, to within a predetermined time period, are treated as related to ventricular activation and are discarded from further analysis. For example there may be a 'blanking period' of 50 ms either side of each ventricular event during which any events in the atrial detection signals are omitted from further analysis. Therefore, if the event in the atrial detection signal is within a predetermined time period of the ventricular event then it is identified as a ventricular event, and the process returns to step 400 to identify another event.

Any event identified in the atrial detection signals, which is not identified as being due to pacing or HFS stimulus artefact, or due to ventricular artefact, is identified as indicative of a true atrial activation and classified as an atrial activation event. In order to reduce the chances of error, if an atrial ectopic is detected then at step 408 the detection algorithm compares the timing of the detected activation in other atrial recordings (A1, A2, . . . , An). An atrial ectopic event will only be registered if present in all, or at least a predetermined number, of the atrial detection signals. This provides additional capability to accurately assess ectopy in the presence of measurement noise.

Once a true atrial ectopic event has been identified, then at step 410, the timings of the event in the different atrial detection signals, together with the locations of the catheter electrodes from which those signals are obtained, are used to determine the position of the source of the atrial ectopic event. Essentially this is done by assuming a constant speed of propagation of activation from the source to the electrodes, and therefore using the timings of the event in the different atrial detection signals to estimate the distance of the source from all of the electrodes. Once the location of the source has been determined, that location is recorded at step 412 on the 3D model of the heart which is stored in the mapping system 112. This can subsequently be used to locate the GP for ablation.

It will of course be appreciated that the various steps in the process of FIG. 4 can be performed in various different orders. Also the effect of omitting the pacing pulses and/or stimulation pulses may be achieved in different ways, such as by actually blanking the detection signals for the periods around the timings of the pacing and stimulation pulses so that the detection signals do not include any identifiable pulses at those times.

When the detectors 106, 108, 110 are in place, the timing and stimulation pulses are transmitted at an appropriate frequency and the detection signals analysed immediately. This allows the stimulation signal to be controlled and modified in response to the detected events, as will now be described.

The process of FIG. 4 may be run continuously with the atrial probe 106 being moved around the left atrium to build up a map of possible GP locations. However continuous stimulation may be undesirable and therefore the control software may be arranged to monitor the results of the event classification process and to control the stimulation signal in response to the results.

Firstly, prior to any attempt at autonomic stimulation, the system may operate in a test mode in which slow (safe) high output pacing pulses may be generated and transmitted on the stimulation channel, without any additional stimulation pulses, for a predetermined period of time, in order to make sure that the ventricle is not within range of the pacing catheter. If a predetermined number of ventricular activation events, which may just be one event, are detected by the software algorithms, using the ECG or ventricular detection signals as described above, then the user is alerted via the user interface 100 and autonomic stimulation is temporarily disabled. If no ventricular events are detected then. The operation of the user interface 100 is described in more detail below.

If no (or less than the predetermined number of) ventricular events are detected in response to the pacing pulses during the test period, then the user interface 100 may be arranged to indicate this to the user, and the software enables the user to select and start one of the detection modes, such as one of the GP detection modes described above, during which the stimulation signal with stimulation pulses with or without the pacing pulses may be started. During the period when the atrium is activating, a short burst or group 302 of high-frequency stimulation pulses 303 are generated to attempt ganglionated plexus stimulation. If a premature atrial ectopic 304*a* is detected, then this is a positive response. The positive response is automatically detected by the signal processing algorithm as described above. Further high frequency stimulation may then be stopped to avoid additional risk of inducing atrial fibrillation, and the user may be alerted to the result via the graphical user interface 100. The user may then move the atrial probe 106 and re-start the pacing pulses to check again for stimulated ventricular activation. If no stimulated ventricular activation is detected in response to the stimulation pulse 302, the high frequency stimulation pulse may be repeated, and the repeating pulses may be continued until a further atrial activation event is detected. If the stimulation signal has been output for a predetermined period, or a predetermined number of pulse groups, without detection of an atrial activation event, then the control software may be arranged to temporarily disable or stop it so as to avoid excessive stimulation which may result in AF, and again this may be indicated to the user via the user interface 100.

Mode 2—Detection of Atrioventricular Node Slowing GPs

When a patient is in atrial fibrillation (AF) the system may be arranged to detect and locate atrioventricular node slowing ganglionated plexus (AVN-GP). In this mode, which again may only be selected via the user interface 100 if the test mode has not detected any ventricular events, if the patient is in atrial fibrillation then a continuous burst of high frequency pulses 303 without pacing pulses 300, is delivered on the stimulation channel 206. If there is an AVN-GP site, then this causes autonomic effects on the atrioventricular node and this, in turn, causes heart rate slowing, which can often result in a long pause in ventricular activation. The software algorithm is therefore arranged in this mode to analyse the detection signals to identify ventricular activation events, as described above, and to analyse the timings of those events. If a pause of at least a predetermined time period, or delay, between consecutive ventricular activation events is detected, which may for example be 2 s or 3 s, then this is taken as indicative of the presence of AVN-GP. In response to the detection of such a pause, the autonomic stimulation signal is stopped and the user is alerted via the computer 102.

Figure 5:
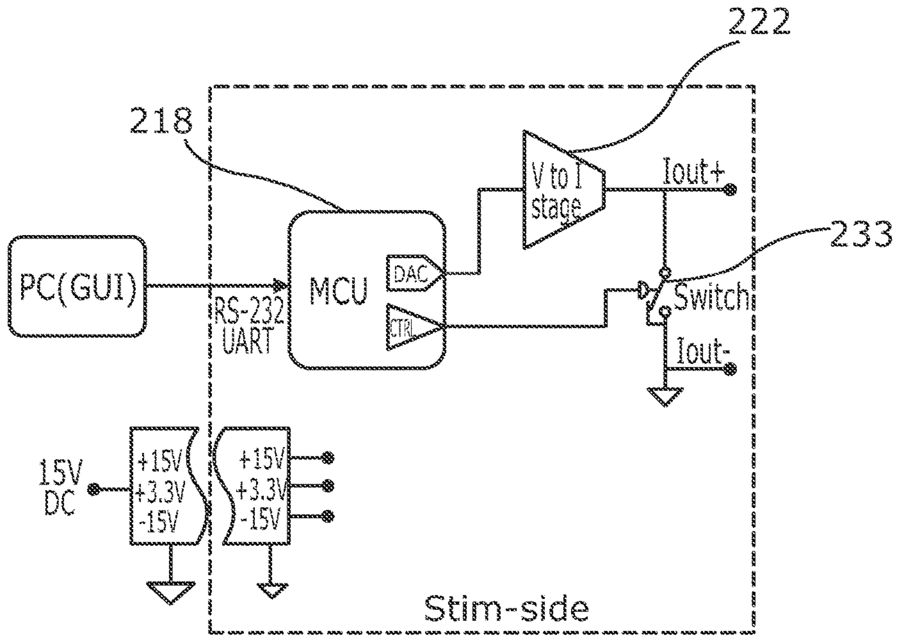
FIG. 5 is a diagram of the stimulation channel of a system according to a second embodiment of the invention.

Referring to FIG. 5, in a modification to the embodiment of FIG. 2 the stimulation channel, as well as including the MCU 218 and the V to I stage 222, includes an impedance control switch 233 connected between the output terminals 224, 226 of the stimulation channel. This switch 233 is controlled by the data controller 202 so that its operation is coordinated with the stimulation signal. The impedance control switch 233 is opened and closed to vary the impedance between the output terminals 224, 226 of the stimulation channel during the stimulation cycle. The switch 233 is opened during the active part of the stimulation cycle, i.e. when the stimulation pulses are being produced to maintain a high impedance between the terminals 224, 226 so that the stimulation current flows through the heart. However during the passive part of the stimulation cycle the switch 233 is closed so as to reduce the impedance between the terminals 224, 226 and reduce the voltage between the terminals 224, 226.

Figure 6:
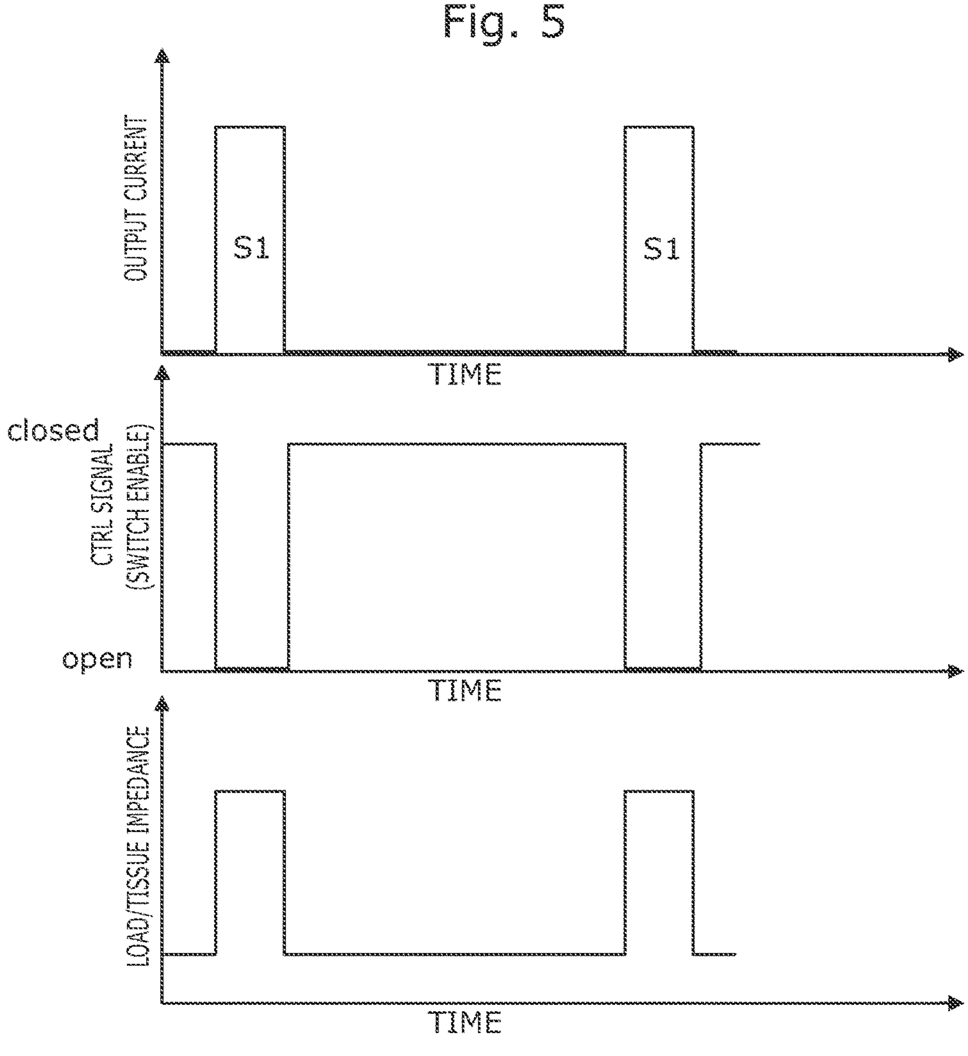
FIG. 6 is a timing diagram showing the operation of the stimulation channel of FIG. 5.

FIG. 6 shows one example of the timing of the impedance control switch 233, in which the switch 233 is opened at the beginning of each pulse S1 in the stimulation signal and closed at the end of each pulse S1 of the stimulation signal. With this approach any signals recorded between the pulses will be attenuated.

Figure 7:
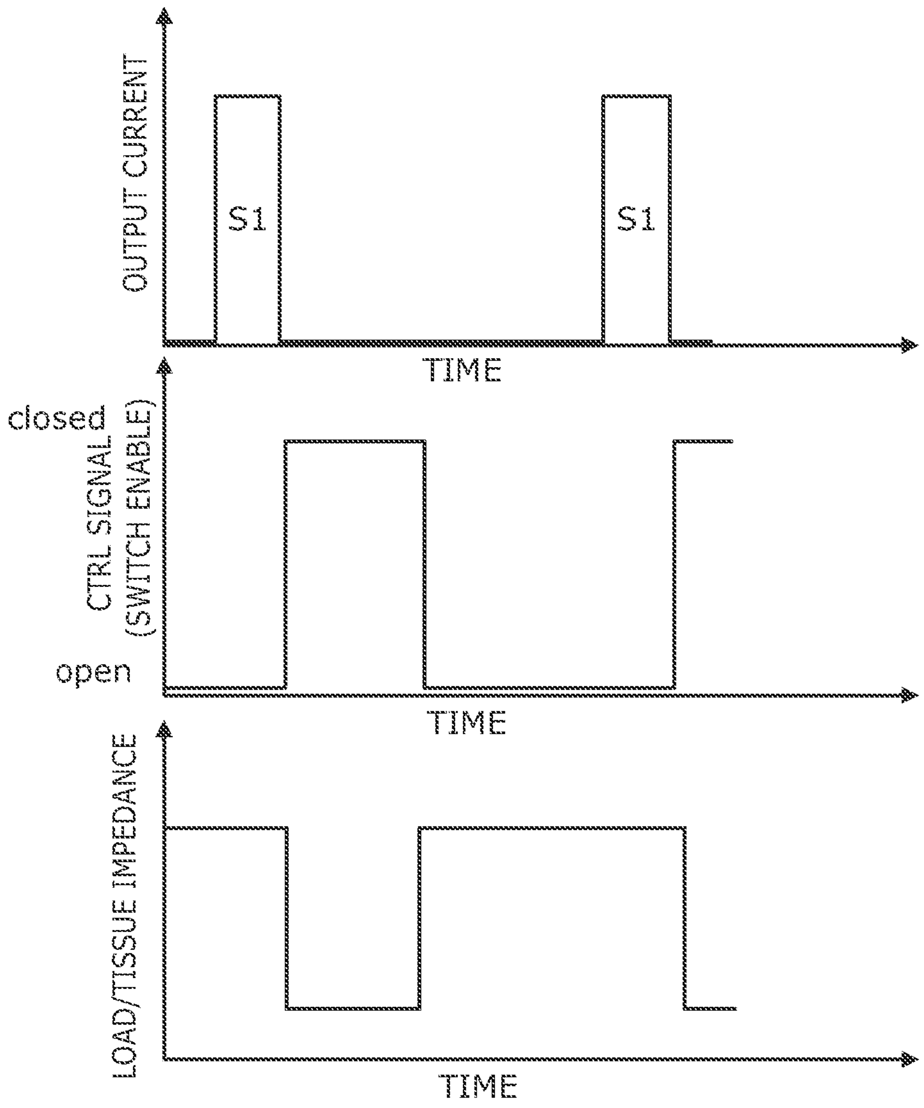
FIG. 7 is a timing diagram showing an alternative operation of the stimulation channel of FIG. 5.

FIG. 7 shows an alternative timing of the impedance control switch 233 in which the switch is closed at the end of each pulse S1 of the stimulation signal, but opened at an intermediate time between consecutive stimulation pulses. This allows a period between the pulses during which signals can be detected without attenuation. The minimum discharge time, for which the switch 233 needs to be closed after each stimulation pulse, will depend on the stimulation pulse width, the output amplifier, the pulse frequency, and the target offset voltage between the electrodes 224, 226.

Figure 8:
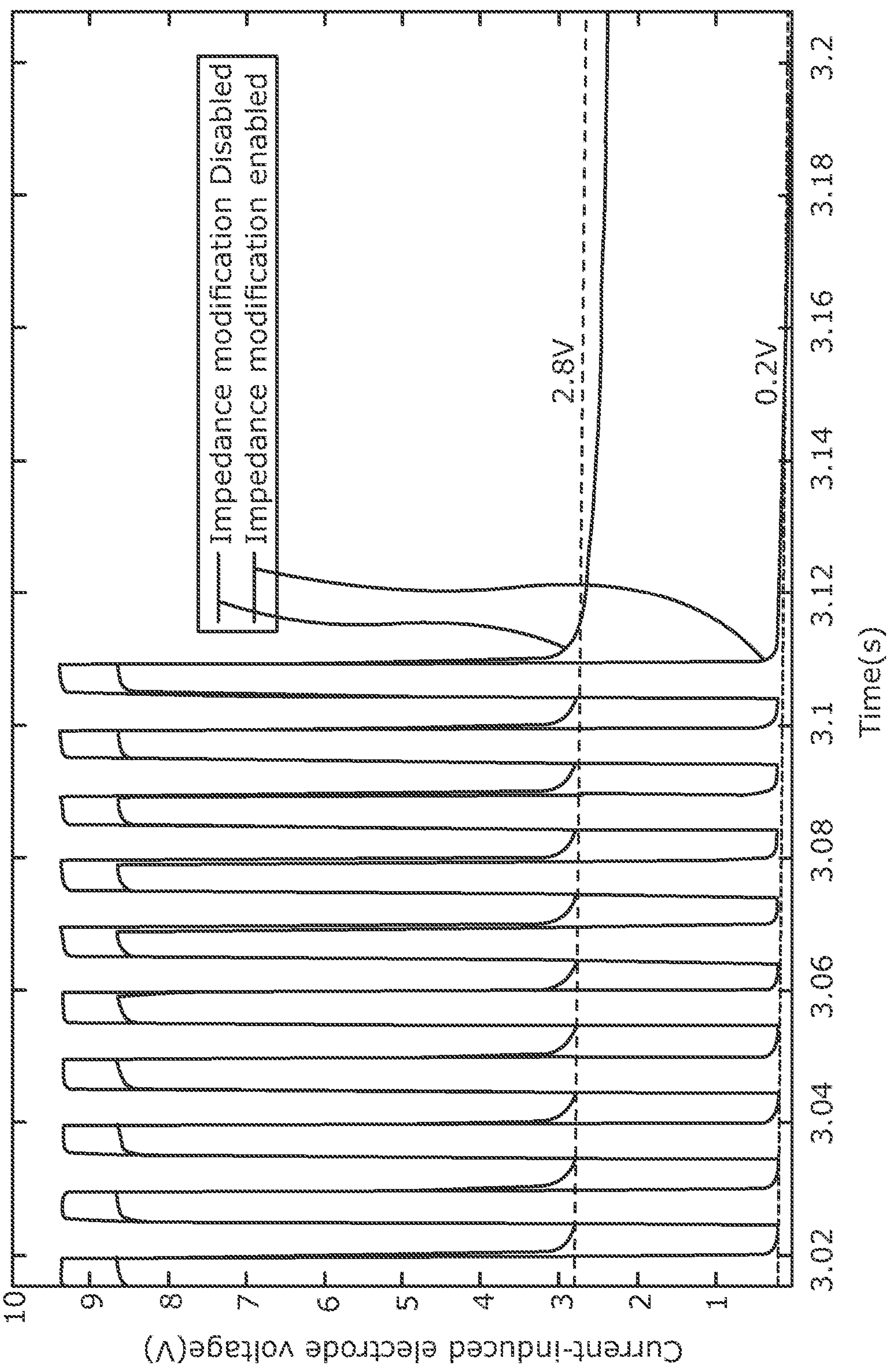
FIG. 8 is plot of current-induced electrode voltage as a function of time in the system of FIG. 1.

Referring to FIG. 8, if the system of FIG. 2 is operated with the impedance modification switch 233 disabled, then the current-induced voltage between the stimulation electrodes falls to about 2.8V between stimulation pulses, whereas with the same stimulation signal, if the impedance modification switch 233 is activated as shown in FIG. 6, the current-induced voltage between the stimulation electrodes falls to about 0.2V between stimulation pulses, and the peak voltage of each pulse is also reduced as a result.

Figure 9:
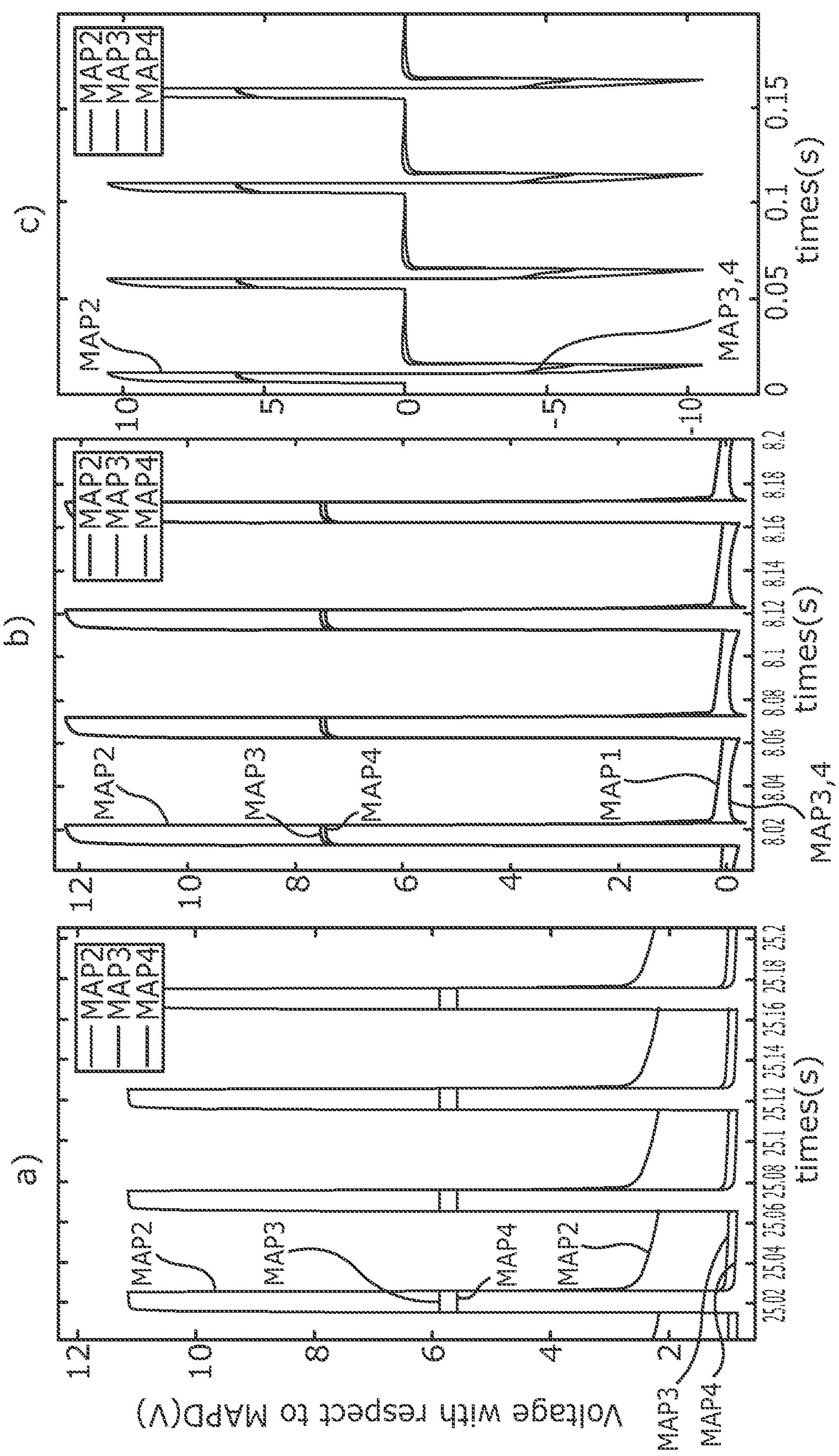
FIG. 9 includes three plots of current-induced electrode voltage in the system of FIG. 1 during three modes of operation.

Referring to FIG. 9, further tests were carried out using the system of FIG. 2 with the impedance modification of FIG. 5 for each of three pulse patterns. In each case the signal from electrode 116*a* at the tip of the probe was used as the reference signal, a stimulation signal was applied to electrode 116*b* and the signals at each of electrodes 116*c*, 116*d* measured relative to that reference as MAP2, MAP3, MAP4 respectively. FIG. 9*a* shows the results for a 10V pulsed signal applied to the stimulation channel using the known Grass system. As can be seen the signal on electrode 116*b* peaked significantly higher than those on the other two electrodes 116*c*, 116*d*, and also remained substantially higher between stimulation pulses. FIG. 9*b* shows the results for a 60 mA 100 Hz square wave applied to the stimulation channel using the system of FIG. 3. As can be seen the signal on electrode 116*b* again peaked significantly higher than those on the other two electrodes 116*c*, 116*d*, but fell to a level closer to the other two electrodes between stimulation pulses. FIG. 9*c* shows the results for a 60 mA biphasic stimulation signal applied to the stimulation channel using the system of FIG. 3. As can be seen the signal on electrode 116*b* again peaked significantly higher than those on the other two electrodes 116*c*, 116*d*, but all three signals retuned to close to zero between stimulation pulses.

Figure 10:
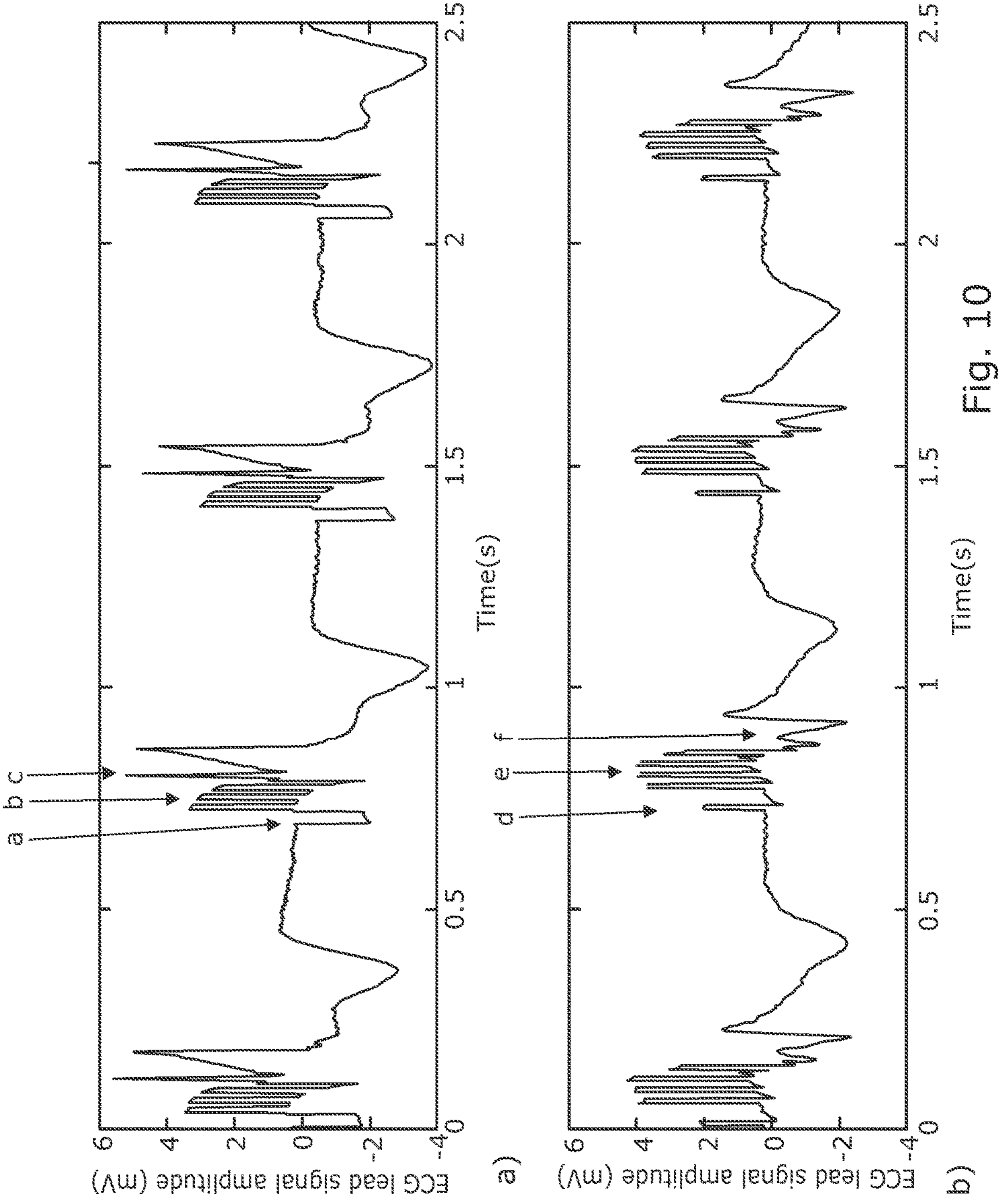
FIG. 10 includes two plots of ECG electrode voltages in the system of FIG. 1.

Referring to FIG. 10, a comparison was made between the signal from an ECG lead as a result of a sequence of timing and stimulation pulses generated using the known Grass system (FIG. 10*a*) and the system of FIG. 3 (FIG. 10*b*). The prominent features of the two plots are as follows. a and d are the pacing pulses. b and e are the HFS stimulation pulses. c and f are the ventricular QRS response. The atrial response is masked by the stimulation pulses due to the placement of the "ECG" leads near the ventricle. It should also be noted that no ectopy is present in FIG. 10*a* or 10*b*. These plots demonstrate that the system of FIG. 3 can output comparable signals to the known Grass system in the same tissue.

Figure 11:
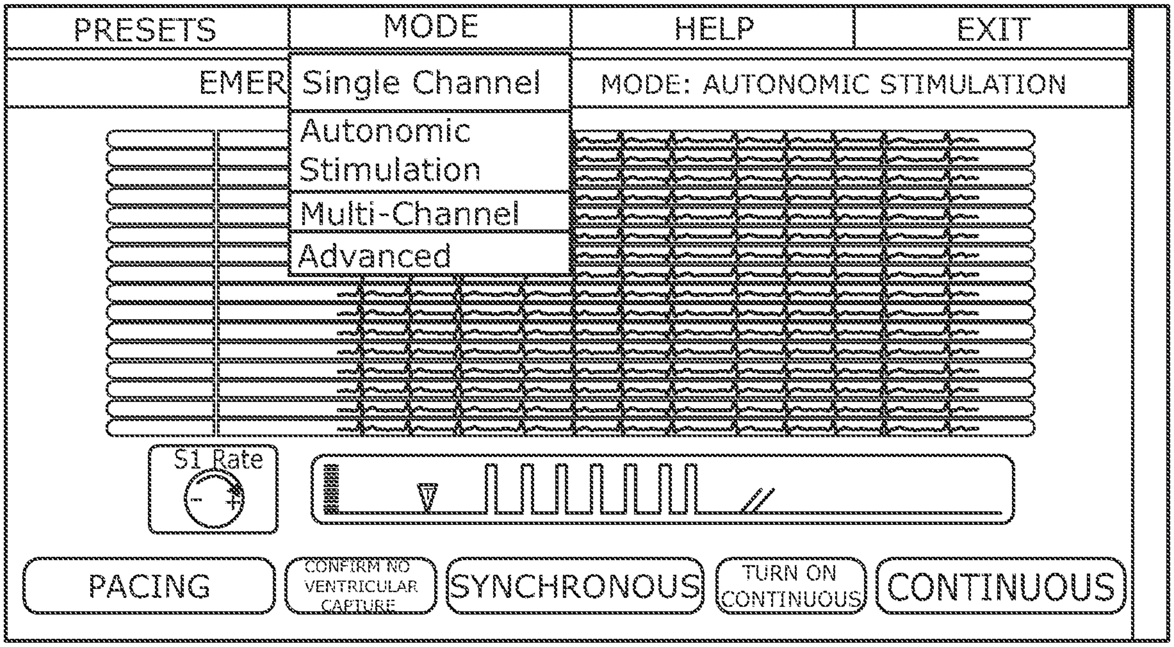
FIG. 11 shows a screen shot of a GUI of the system of FIG. 1.
Figure 12:
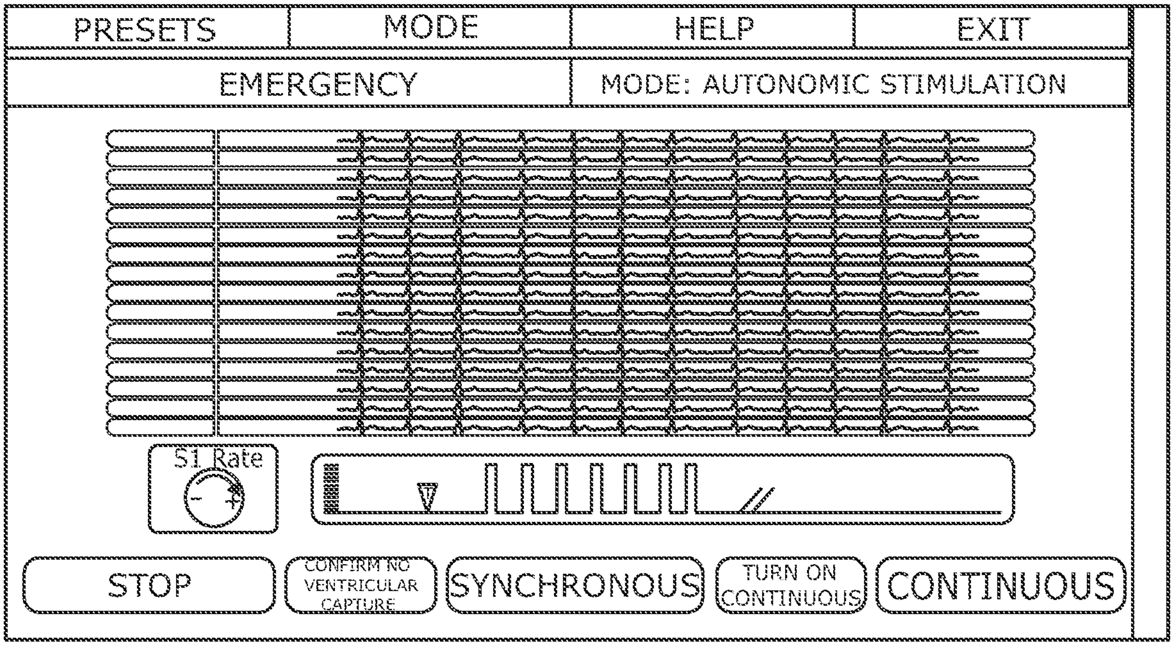
FIG. 12 shows a further screen shot of the GUI of the system of FIG. 1.
Figure 13:
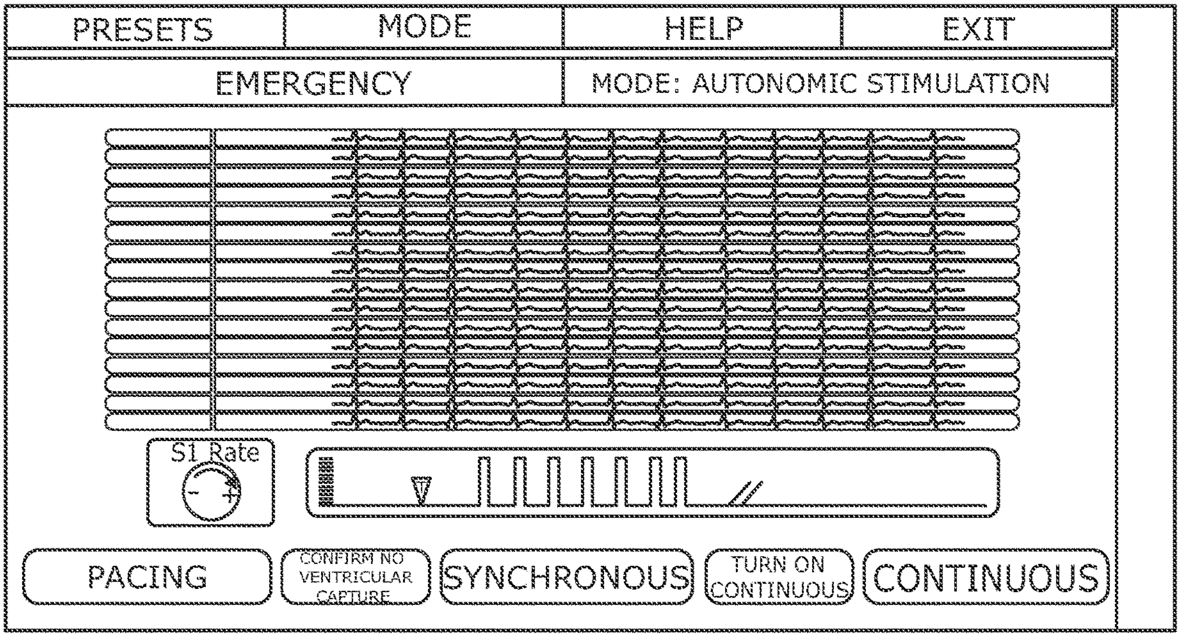
FIG. 13 shows a further screen shot of the GUI of the system of FIG. 1.

Referring to FIGS. 11 to 13, the graphical user interface (GUI) may take a variety of forms and may be arranged, as described above, to direct the user through various steps during operation of the system. Referring to FIG. 11 the GUI may for example allow a user to select autonomic stimulation from a list of mode options, which may also include other more conventional modes of operation. If autonomic stimulation is selected, then the GUI does not provide an option to select synchronous or continuous stimulation, but only presents a pacing option which, if selected, starts the system in the test mode in which just a sequence of pacing pulses is produced in the stimulation channel. The signals on the detection channels may be displayed on the GUI to enable the user to determine whether any ventricular response is produced. In the example shown there are 16 detection channels each showing just a sequence of pacing pulses. This indicates that there is no ventricular response. This can be confirmed also by the software algorithms which may be arranged to detect ventricular activation as described above. After the test mode has been run for a predetermined period, the GUI may give the user the option to confirm that there has been no ventricular activation. In response to that confirmation the GUI may switch to the screen of FIG. 13 from which the user can select synchronous or continuous stimulation and set the parameters of those modes, such as the frequency and duration of the pulses.

The autonomic stimulation options may be made available to a user of the system only on certain conditions. For example the conventional modes of operation mentioned above with reference to FIG. 10 may always be available, but access to the autonomic stimulation options may controlled by the system software or other methods. This allows the autonomic stimulation options to be made available only to selected users, or only on payment made for use of those options.

Figure 14:
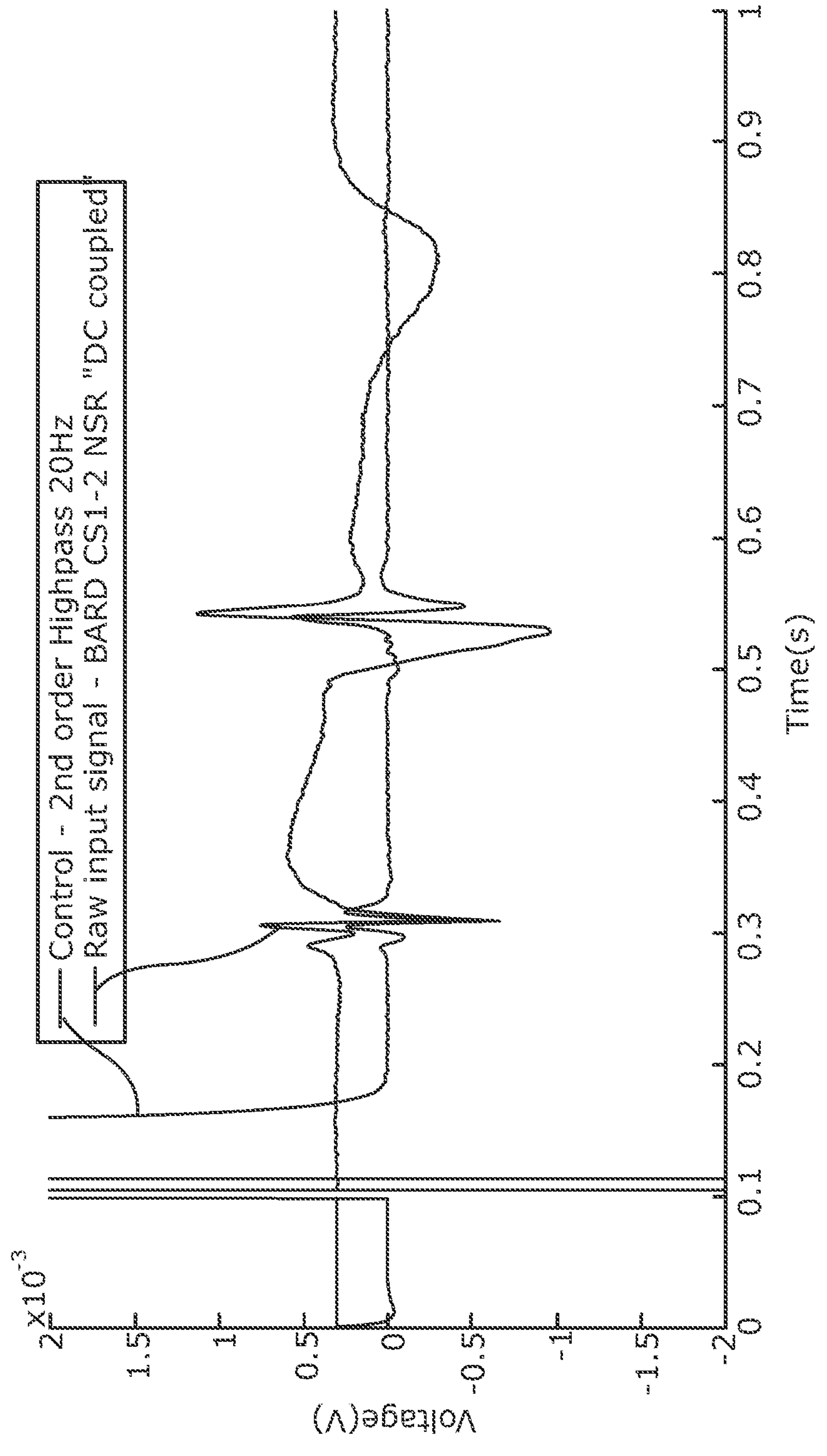
FIG. 14 is a plot of a simulated raw measured detection signal and a filtered detection signal in the system of FIG. 2.
Figures 15A, 15B:
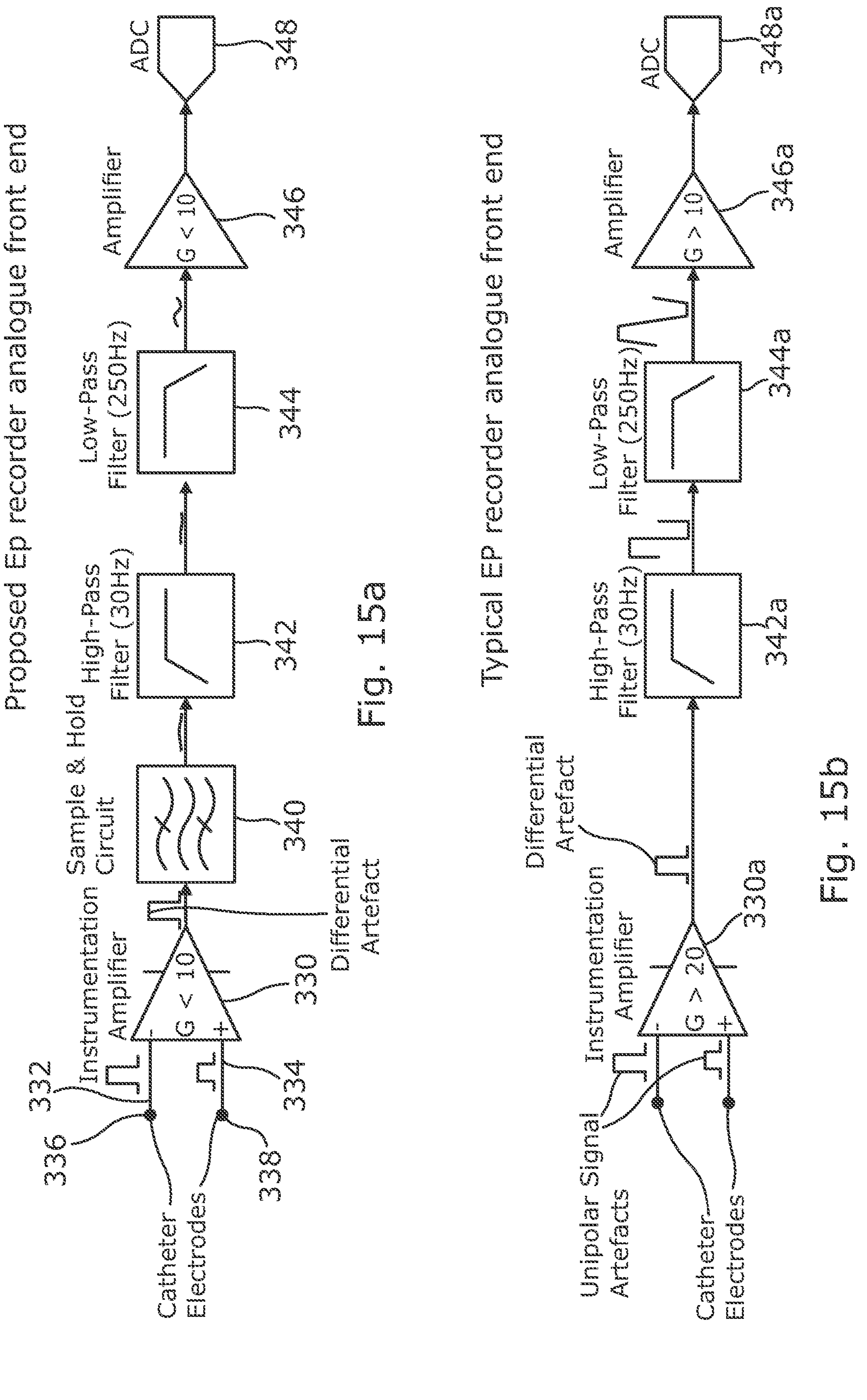
FIG. 15*a* is a diagram of a detection channel use in a simulation.
FIG. 15*b* is a diagram of a detection channel of a typical electrophysiological system for comparison.

Cardiac stimulation as described above can cause disruptive artefact on the recording of intracardiac electrical signals. This is made worse in the presence of filtering that is intended to remove noise. The filters take time to settle and have transient properties that are not favourable in the presence of a non-physiological high amplitude pacing signal. FIG. 14 shows a simulated raw measured signal including a pacing pulse at time 0.1 s followed by pulses produced by activation, together with a simulated filtered version of the same signal. The amplitude of the pacing pulse is 10V whereas the amplitude of the activation pulses is of the order of 1 mV. It can be seen that the filtered signal takes a significant time, about 0.1 s, to return to baseline after the pacing pulse, which itself only lasts about 10 ms. During high frequency stimulation there may only be about 30 ms between stimulation pulses and so this long settling time would interfere significantly with the detection of activation pulses between the stimulation pulses. It is therefore advantageous to include in the stimulation and recording system one or more mechanisms to remove these stimulation artefacts. Optionally, after removal of the pacing artefact, an analogue copy of the post-processed signal may be outputted, for example through the pre-gain outputs shown in FIG. 2, and used as an input to other external recording systems, thus enabling retro-fitting of all artefact reduction capabilities onto existing EP recorders. Oversampling (≥4 KSPS) and high resolution ADC/DAC (≥16-bit) systems may be used to achieve high-fidelity analogue output when artefact reduction is performed digitally. Various removal methods will be described below. Each of these may be provided as separate module between the input terminal(s) 236, 238, 256 and the other components of the detection channels shown in FIG. 2, or between those components and the data controller 202, or may be incorporated with the filtering and amplification components or the data controller as appropriate depending on whether they involve analogue filtering, analogue amplification, or digital signal processing.

ANALOGUE METHODS

Voltage Limiter/Clamping Circuit

This circuit is arranged to operate in two modes a) As a normal amplifier with gain 1-100× when its input voltage |Vin|<Vth b) As a voltage clamp at a pre-determined level Vc when |Vin|>Vth where Vc=Vth*Amplifier Gain. The threshold voltage Vth may be set to a level well above the amplitude of intra-cardiac signals and hence would be exceeded only during stimulation. The input signal should be AC-coupled or bipolar to prevent undesired clamping from excessive DC-offset drift.

Non-Linear Filter

An analogue filter that operates in two modes a) Normal filter when |Vin|<Vth b) Voltage clamp at a pre-determined level Vc when |Vin|>Vth Such a filter would retain all relevant filter characteristics during normal recordings but make use of internal diodes to improve the transient characteristics immediately after stimulation. Vth characteristics would be identical to the voltage limiter circuit. A suitable circuit is described in Texas Instruments (2019). Fast-settling low-pass filter circuit. Analog Engineer's Circuit: Amplifiers. SBOA244—January 2019 http://www.tij.co.jp/jp/lit/an/sboa244/sboa244.pdf Automatic Gain Control A gain-stage that operates in two modes:

a) High-gain: Gain ranging from 1-100× b) Low-gain: Gain ranging from 0.001-1×

High-gain mode may be used when recording normally for optimal signal-to-noise performance. Low-gain mode would be employed only during stimulation to prevent amplifier saturation and improve transient performance; by limiting the amplitude of all fast transitions induced by stimuli.

Hardware Blanking

The analogue inputs may be disconnected during stimulation using an analogue switch. They may be left floating or connected to a fixed external potential.

Sample and Hold

The analogue inputs may be connected to a sample and hold circuit. The input will be tracked during normal recording and held at the pre-stimulation potential during stimulation.

Closed-Loop Recorder Feedback

Use the artefact-affected output of a recording channel synthesize a digital "artefact estimation" signal containing only the observed artefact. Generate the analogue artefact estimation signal via means of a digital to analogue converter. Subtract, in analogue using a differential amplifier, the artefact estimation signal from subsequent inputs to the recording channel during stimulation.

DIGITAL METHODS

Basic Software Blanking

Set all data acquired during stimulus output to 0 amplitude.

Software Blanking with Digital Sample and Hold

Set all data acquired during stimulus output to the last acquired sample amplitude before stimulation. Alternatively use an average amplitude from a set of the last acquired pre-stimulation samples.

Software Blanking with Linear Interpolation

Set all data acquired during stimulus output to a value interpolated using the last acquired pre-stimulation sample and the first acquired post-stimulation sample. Alternatively use an average amplitude from a set of the last acquired pre-stimulation samples/first acquired post-stimulation samples.

Digital Band-Pass Filter

Low-pass filter to attenuate high-frequency components of stimulation artefact, and high-pass filter to attenuate any residual DC offsets, with cut-off frequencies of both optionally being tuned during stimulation to improve artefact suppression performance at the expense of recorded bandwidth. Wideband analogue filtering (DC of frequencies between 0.05 Hz to $F_{sampling}/2$ where $F_{sampling}$ is the digital sampling frequency of the analogue signal) may be employed to enable maximal manipulation of the signal bandwidth.

Digital Notch Filter Same as analogue notch filter described above but implemented through DSP (IIR/FIR).

Comparison with Other Channels

Record simultaneously from the same electrode with two channels; one which does and one which does not employ any of the analogue or digital methods described. Alter parameters of the artefact reduction method employed using the similarity between the two recorded signals.

For example when blanking:

If the two channels both appear saturated immediately after stimulation, increase the blanking interval to improve settling time on the artefact reduction channel.

Figure 16A:
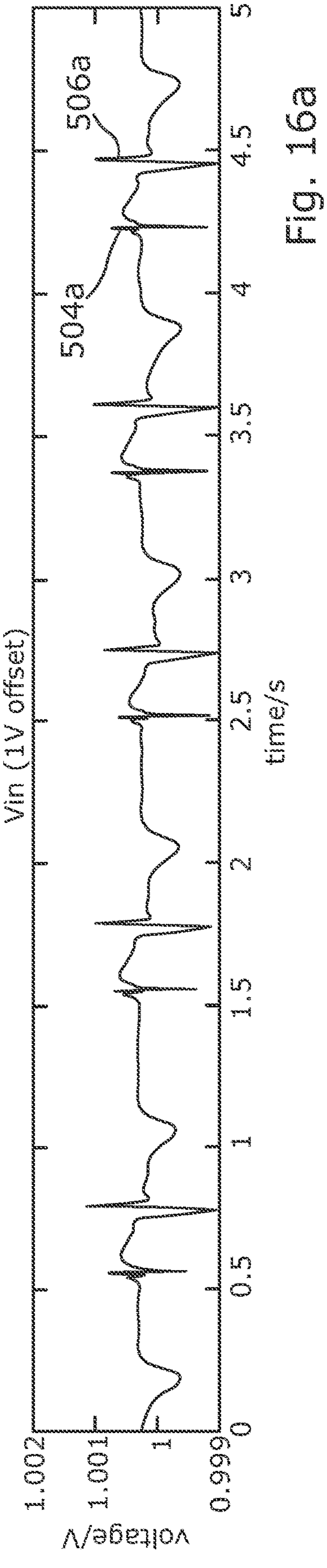
FIG. 16*a* is a detection signal used in a simulation of the system of FIG. 15*a;*
Figure 16B:
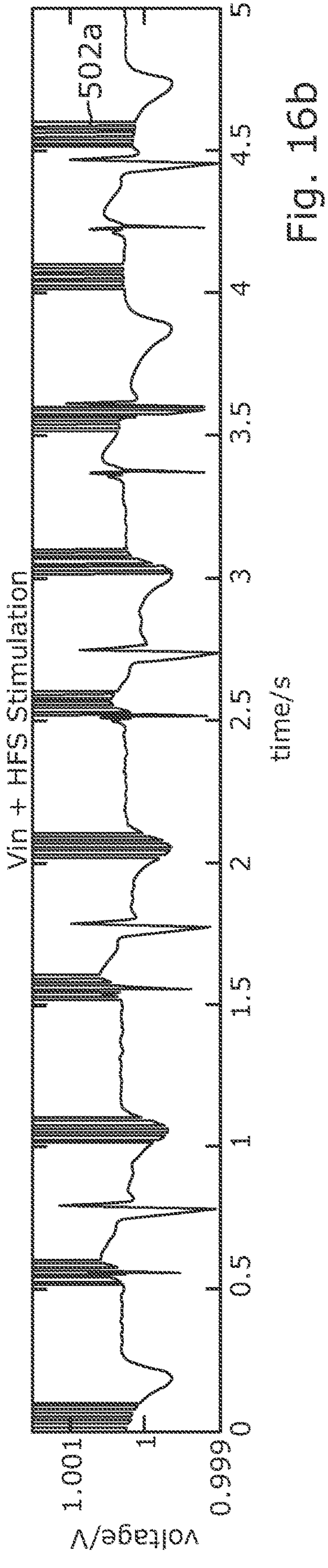

Referring to FIG. 16*a*, a detection channel used in a simulation of an embodiment of the invention comprises a differential amplifier 330, having two inputs 232, 234 each connected to a respective one of two input terminals 336, 338 of the channel, and an output in the form of a difference signal that varies with the difference between the signals on the two input terminals 336, 338. The channel further comprises a sample and hold circuit 340 for artefact reduction by disconnecting the analogue front-end filter inputs from the rest of the circuit during stimulation as described above, and a high pass filter 342 and low pass filter 344. Finally the channel comprises an amplifier 346 and an ADC 348. Referring to FIG. 16*b*, the conventional channel comprises the same components which are indicated by the same reference numerals superseded by the letter 'a'. The sample and hold circuit 340 is not present in the conventional channel. Apart from that, the main difference is the reduced front-end gain in the channel of FIG. 16*a* to prevent amplifier/ADC saturation (this is compensated for by using high-resolution ADC as described above).

Figure 16C:
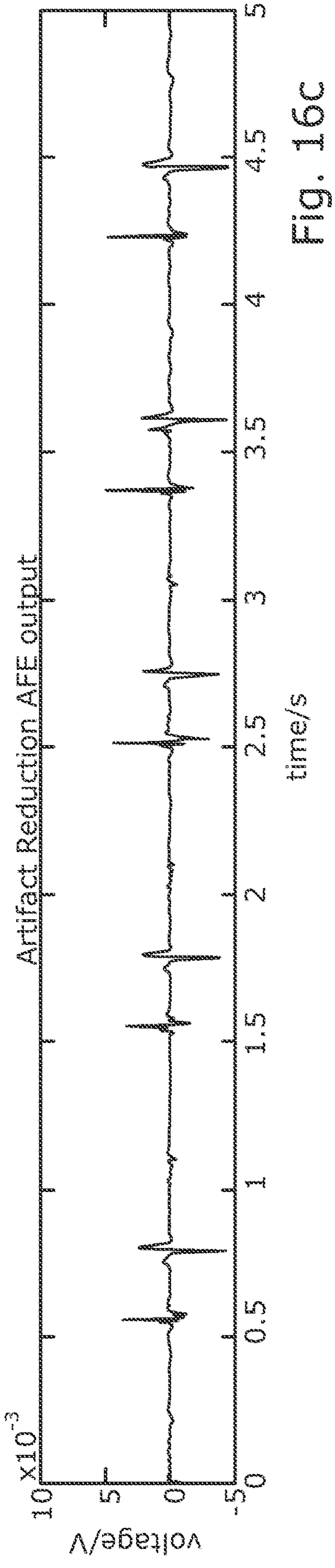
FIG. 16*c* is the corresponding simulated output of the system of FIG. 15*a;*

Referring to FIG. 16*a* simulated ectopic pulses 504*a* and simulated ventricular pulses 506*a* (with a 1V offset to show that the method is not affected by large input DC offsets which may be induced during stimulation). Referring to FIG. 16*b*, HFS stimulation pulses 502*a* are also added into the simulated input signal. The simulated output signal is shown in FIG. 16*c*.

Figures 17A, 17B, 17C:
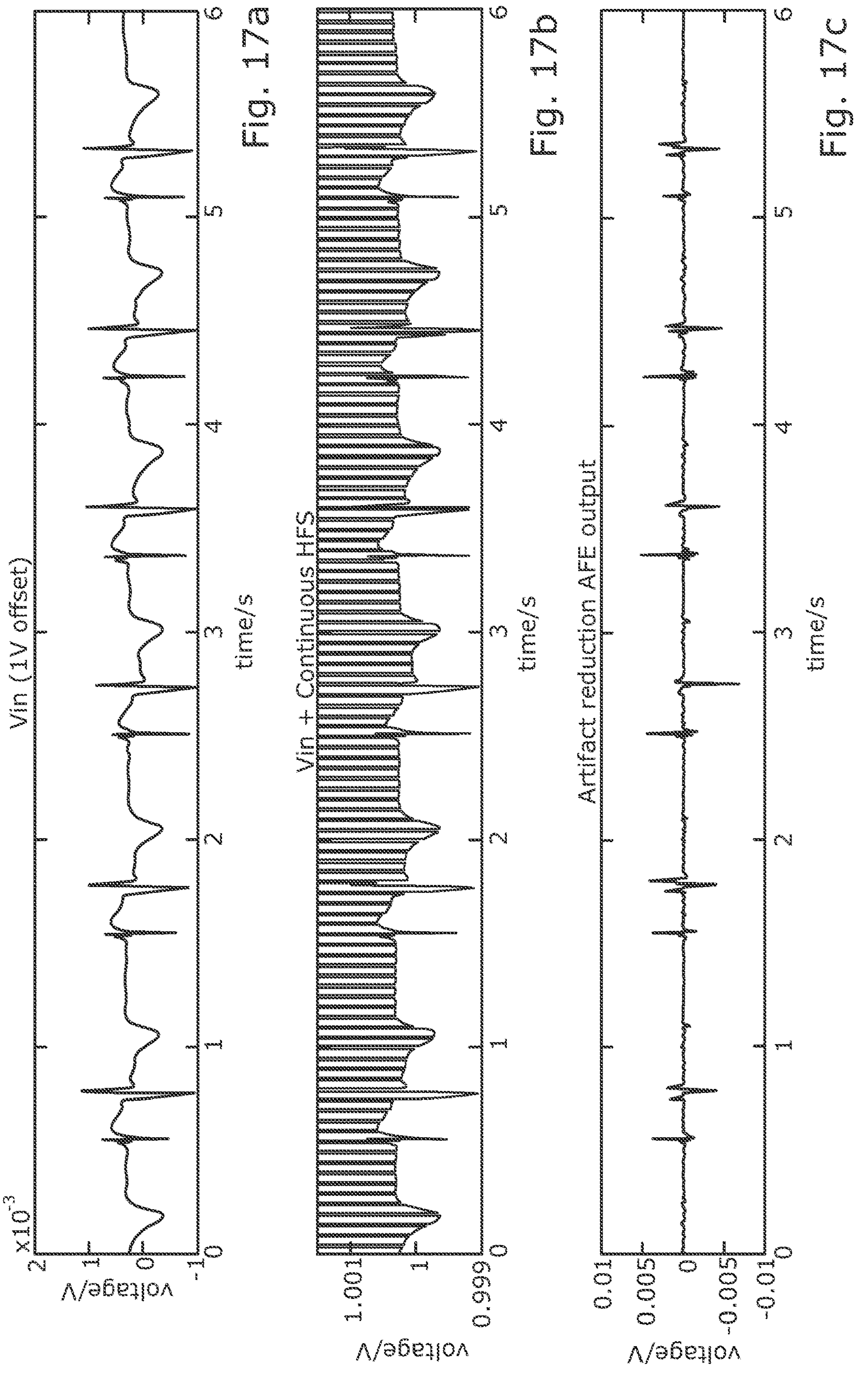

Referring to FIG. 17*a*, in a second simulation, the simulated ectopic pulses 504*a* and simulated ventricular pulses 506*a* (again with a 1V offset) were first generated, but then a continuous series of HFS stimulation 508 was introduced into the input signal. The simulated output signal is shown in FIG. 1*c*.

In both of these simulations it can be seen that the ectopic and ventricular pulses are clearly extracted so that the analysis such as that described above with reference to FIG. 4 can be carried out.

The invention claimed is:

1. Apparatus for electrophysiological studies, the apparatus comprising:

at least one output channel;

a plurality of detection channels each configured to carry a respective detection signal; and a controller, wherein the at least one output channel includes a stimulation channel, the detection channels include an atrial channel and at least one reference channel the controller is configured to provide a stimulation signal to the stimulation channel, wherein the stimulation signal is configured to trigger ectopy events and comprises a plurality of high frequency stimulation pulses, the stimulation pulses being arranged in groups, and to receive the detection signals from the atrial channel after each of the groups of stimulation pulses and to process the detection signals thereby to identify, in the detection signals, ectopy events triggered by the stimulation signal; and the controller is configured to process the detection signal received from the at least one reference channel after each of the groups of stimulation pulses, to identify ventricular activation events, thereby to distinguish between ventricular activation events and ectopy events in the detection signal from the atrial channel;

the controller is further configured to stop producing the stimulation signal in response to a count of detected ectopy events increasing to a predetermined number; and wherein the stimulation signal is applied across two stimulation electrodes and the controller is arranged to control the impedance between the stimulation electrodes between the stimulation pulses thereby to control an offset voltage between the electrodes.

2. Apparatus according to claim 1 wherein the controller is further configured to identify ventricular activation events in the detection signals.

3. Apparatus according to claim 1 wherein the controller is configured to process the detection signals to produce an outcome and to control the stimulation signal in response to the outcome.

4. Apparatus according to claim 1 further comprising:

an atrial catheter, the atrial catheter comprising at least one atrial electrode, wherein the atrial channel is connected to said at least one atrial electrode; and a ventricular catheter, the ventricular catheter comprising at least one ventricular electrode, wherein one of the at least one reference channels is connected to said at least one ventricular electrode.

5. Apparatus according to claim 1 further comprising an ECG electrode set wherein one of the at least one reference channels is connected to the ECG electrode set.

6. Apparatus according to claim 1 wherein the at least one output channel includes a pacing channel and the controller is configured to:

provide a pacing signal to the pacing channel, identify ventricular activation events that are caused by the pacing signal and to modify or stop the pacing signal in response to the identification of a predetermined number of ventricular activation events that are identified as caused by the pacing signal;

perform a ventricular activation test in which the pacing signal is output without the stimulation signal; and enable the stimulation signal only after the ventricular activation test has been passed.

7. Apparatus according to claim 1 wherein the controller is arranged to process the detection signals to identify two consecutive ventricular events, to measure a delay between said consecutive ventricular events, and to determine whether the delay exceeds a predetermined time period.

8. Apparatus according to claim 1 wherein the at least one output channel includes a pacing channel and the controller is configured to provide a pacing signal to the pacing channel;

the pacing signal comprises a pacing pulse preceding each of said groups of stimulation pulses.

9. Apparatus according to claim 8 wherein the controller is operable in an ectopy triggering mode in which the system is arranged to produce the pacing pulses and the groups of stimulation pulses, and an atrioventricular node slowing mode in which the system is arranged to produce the stimulation pulses without the pacing pulses.

10. Apparatus according to claim 9 wherein the controller comprises a user interface arranged to enable a user to select one of the modes and to adjust at least one parameter of the stimulation signal or the pacing signal.

11. Apparatus according to claim 10 wherein the controller is configured to perform a ventricular activation test in which the pacing signal is output without the stimulation signal, and the user interface only enables a user to start the stimulation signal after the ventricular activation test has been completed.

12. Apparatus according to claim 1 wherein each of the stimulation pulses is a bipolar voltage pulse.

13. Apparatus according to claim 1 wherein the controller is arranged to define a target current and to control the stimulation signal during each of the stimulation pulses to achieve the target current.

* * * * *